(12) United States Patent
Blank

(10) Patent No.: US 10,855,207 B2
(45) Date of Patent: Dec. 1, 2020

(54) ELECTRIC LINEAR REPETITIVE PULSED DRIVE FOR OPERATING EQUIPMENT

(71) Applicant: ETO MAGNETIC GmbH, Stockach (DE)

(72) Inventor: Anton Blank, Stuttgart (DE)

(73) Assignee: ETO MAGNETIC GmbH, Stockach (DE)

( * ) Notice: Subject to any disclaimer, the term of this patent is extended or adjusted under 35 U.S.C. 154(b) by 0 days.

(21) Appl. No.: 16/087,745

(22) PCT Filed: Mar. 27, 2017

(86) PCT No.: PCT/EP2017/057181
§ 371 (c)(1),
(2) Date: Sep. 24, 2018

(87) PCT Pub. No.: WO2017/167684
PCT Pub. Date: Oct. 5, 2017

(65) Prior Publication Data
US 2019/0109546 A1   Apr. 11, 2019

(30) Foreign Application Priority Data
Mar. 27, 2016   (DE) .................. 10 2016 003 599

(51) Int. Cl.
*H02N 2/06*   (2006.01)
*H01L 41/12*   (2006.01)
(Continued)

(52) U.S. Cl.
CPC ............ *H02N 2/067* (2013.01); *A45D 26/00* (2013.01); *A61C 17/34* (2013.01); *A61H 39/08* (2013.01);
(Continued)

(58) Field of Classification Search
CPC ........ H02N 2/067; H02N 2/043; A45D 26/00; A61C 17/34; A61H 39/08;
(Continued)

(56) References Cited

U.S. PATENT DOCUMENTS 5,096,643 A   3/1992   Kowanz et al.
6,515,382 B1   2/2003   Ullakko
(Continued)

FOREIGN PATENT DOCUMENTS

CN   101264020 A   9/2008
CN   104769271 A   7/2015
(Continued)

OTHER PUBLICATIONS

International Search Report dated Jun. 7, 2017 issued in corresponding international patent application No. PCT/EP2017/057181.
(Continued)

*Primary Examiner* — Mohamad A Musleh
(74) *Attorney, Agent, or Firm* — Posz Law Group, PLC

(57) ABSTRACT

An electric linear repetitive pulsed drive for an operation of apparatuses, in particular for an operation of apparatuses for improving an efficiency of which a working energy that is output in a pulsed manner, with at the same time low repetition frequencies, is advantageous, includes a magnetic circuit with an air gap and an electric coil, a magnetic shape-memory adjustment element and a reset unit, and a control electronics unit, wherein the electric linear repetitive pulsed drive outputs its energy in discrete-time fashion, bundled in short time intervals, that is in pulses.

14 Claims, 1 Drawing Sheet

Figure 1:
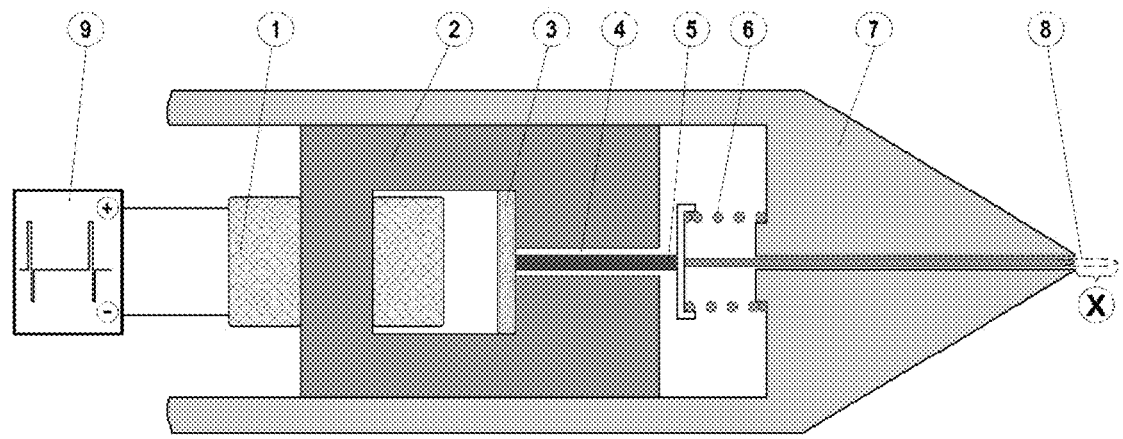

(51) Int. Cl.
| | |
|---|---|
| *F03G 7/06* | (2006.01) |
| *A61N 1/36* | (2006.01) |
| *A45D 26/00* | (2006.01) |
| *A61C 17/34* | (2006.01) |
| *A61H 39/08* | (2006.01) |
| *A61M 37/00* | (2006.01) |
| *H01L 41/04* | (2006.01) |
| *H02N 2/04* | (2006.01) |

(52) U.S. Cl.
CPC ..... *A61M 37/0076* (2013.01); *A61N 1/36017* (2013.01); *F03G 7/065* (2013.01); *H01L 41/042* (2013.01); *H01L 41/12* (2013.01); *H02N 2/043* (2013.01); *A61H 2201/123* (2013.01)

(58) Field of Classification Search
CPC ......... A61H 2201/123; A61M 37/0076; A61N 1/36017; F03G 7/065; H01L 41/042; H01L 41/12
See application file for complete search history.

(56) References Cited

U.S. PATENT DOCUMENTS

| | | | |
|---|---|---|---|
| 2004/0145435 A1* | 7/2004 | Ohta | H01L 41/12 335/78 |
| 2005/0256448 A1 | 11/2005 | Angel et al. | |
| 2006/0144472 A1 | 7/2006 | Ullakko et al. | |
| 2008/0228212 A1 | 9/2008 | List | |
| 2009/0033448 A1* | 2/2009 | Hoang | F02M 51/0603 335/215 |
| 2010/0242673 A1 | 9/2010 | Laufenberg | |
| 2011/0179790 A1* | 7/2011 | Pretorius | F03G 7/065 60/641.15 |
| 2011/0315903 A1* | 12/2011 | Sohn | F03G 7/065 251/11 |
| 2012/0291778 A1 | 11/2012 | Nagel et al. | |
| 2015/0207059 A1 | 7/2015 | Laufenberg et al. | |
| 2015/0292456 A1 | 10/2015 | Beier et al. | |
| 2016/0148736 A1 | 5/2016 | Schlepp et al. | |
| 2017/0281459 A1 | 10/2017 | Cirillo-Schmidt | |

FOREIGN PATENT DOCUMENTS

| | | |
|---|---|---|
| DE | 39 17 423 C1 | 5/1990 |
| DE | 40 02 199 A1 | 7/1991 |
| DE | 601 07 364 T2 | 5/2005 |
| DE | 10 2005 038 891 A1 | 2/2007 |
| DE | 10 2013 107 744 A1 | 1/2015 |
| EP | 1 197 702 B1 | 11/2004 |
| JP | H04-253888 A | 9/1992 |
| JP | H04-253889 A | 9/1992 |
| WO | 2014/019738 A1 | 2/2014 |
| WO | 2016/038028 A1 | 3/2016 |
| WO | 2016046142 A1 | 3/2016 |
| WO | 2018219912 A1 | 12/2018 |

OTHER PUBLICATIONS

International Preliminary Report on Patentability dated Oct. 2, 2018 issued in corresponding international patent application No. PCT/EP2017/057181.
Office Action dated Jun. 14, 2019 issued in corresponding CN Patent Application No. 201780020635.X (and English anslation).
Office Action dated Feb. 6, 2020 issued in corresponding CN Patent Application No. 201780020635.X(and English summary).
Tu Fuquan et al., Design and Simulation of New Type Servo Valve Actuator, Jul. 2014, vol. 42, No. 13, College of Machinery and Automation, Wuhan University of Science and Technology, Wuhan, China (with English abstract).
Office Action dated Oct. 23, 2019 issued in corresponding EP Patent Application No. 17 713 659.5 (and English translation).
Wang et al., "Actuation Principle and Property of Magnetically Controlled Shape Memory Alloy Actuators." Proceedings of the 2005 IEEE International Conference on Mechatronics. Jul. 10-12, 2005. Taipei, Taiwan.
Office Action dated Dec. 21, 2018 in corresponding DE patent application No. 10 2016 003 599.4 (and English translation).
Office Action dated Jul. 20, 2020 in corresponding DE patent application No. 10 2016 003 599.4 (and English translation).
Intention to Grant dated May 25, 2020 in corresponding EP application No. 17713659.5.

* cited by examiner

ELECTRIC LINEAR REPETITIVE PULSED DRIVE FOR OPERATING EQUIPMENT

CROSS REFERENCE TO RELATED APPLICATIONS

This application is a U.S. national stage application of PCT/EP2017/057181 filed on Mar. 27, 2017, which is based on German Patent Application No. 10 2016 003 599.4 filed on Mar. 27, 2016, the contents of which are incorporated herein by reference.

The invention concerns an electric linear repetitive pulsed drive for operating equipment for improving an efficiency of which equipment a working energy that is output in a pulsed manner, with at the same time low repetition frequencies, is advantageous.

To illustrate electric apparatuses which are improvable by the present patent application, the following may be named as examples: devices pricking into organic skin or inserting substances into organic skin by pricking, e.g. for permanent make-up, tattoos, microblading, mesotherapy, micro-needling, stimulation therapy, scar treatment, insertion of natural body substances, like hyaluronic acid, collagen, etc., wherein it is in such devices the easier possible to overcome skin elasticity the higher the prick-in velocity, and the sensitivity of the skin permits only low repetition frequencies for a mechanical treatment, as otherwise too large wounds and consequent scars may occur: and, as further examples, shaver apparatuses, haircutters, epilator apparatuses, in which a high cutting or plucking velocity will bring about a low-pain application which, with prior art apparatuses, would only be achievable, like in the example given above, with high repetition frequencies, resulting in too fast heating-up, heavy vibrations, huge noise production and, insofar as they are battery/accumulator-driven devices, in a fast discharge of the accumulator/battery due to the huge power demand; and, to give further examples, dental cleaning apparatuses, manicure devices, pedicure devices, as the working velocity of the drive results, for example, in essentially shortened treatment time and the low repetition frequency results in a more gentle treatment.

PRIOR ART

Electric linear drives. i.e. drives which are not rotating but repetitive on a movement axis, are usually based on linear electro-magnetic pull/push magnets or on rotating motors the rotation of which is converted into a linear movement via a gearing. While further operating principles, like the piezo-electric operating principle, the magnetostrictive operating principle or the electrostatic operating principle, achieve the desired high velocities of less than 1 ms (1 millisecond) per work stroke, their travel distance is too small for the applications or their price is too high for mass production. On the other hand, the thermal operating principle and the shape-memory effect achieve the desired larger distances of more than 0.5 mm, however with a working velocity that is too low by far.

The drives for electrically generating linear repetitive movements which are generally in use nowadays, namely electromagnetic pull/push magnets, oscillate, due to their structure as a mass-spring system or as rotating electric motors with a gearing, in a time continuum following an approximately sinus-shaped path-time diagram. All movement parameters are hence distributed over time, in a continuous-time manner, in an approximately sinus-shaped fashion, on account of which a concentration of the input energy into a short time period with a high velocity is not possible, which means that short, quick discrete-time movements are not possible on principle, except by increasing a repetition frequency, which would in these applications lead to major disadvantages, e.g. heating up, noise production, vibrations.

The only electric linear repetitive drives meeting the stroke and velocity requirements at a mass-production competitive price are electric tilt armatures, respectively flat-armature magnets. In both, rather similar functionalities a magnetic circuit is closed by a pull on a ferromagnetic armature member, as a result of which the armature is disproportionately accelerated until impacting onto the stator, thus achieving sufficiently high velocities and strokes. Abrupt braking of the armature when impacting on the stator deletes a large portion of the electrically introduced motion energy in a very short time, thus generating correspondingly loud noise, which is not acceptable for the aforementioned practical applications. If the impact of the armature is damped, e.g. by means of elastic materials or springs, the advantages of the principle get lost as, due to the small strokes of approximately 0.5 to 1.5 mm, only short brake paths are possible and the greatest possible velocity is thus drastically reduced for the sake of a reduced noise production.

The already known and applied operating principles of electric linear repetitive drives with a continuous-time energy output lead to limited velocities, restricted strokes or inacceptable noise production, and thus result in a limited performance of the apparatuses driven with said operating principles.

Advantages of the Invention

It is an objective of the invention to create an electric linear repetitive drive which provides a pulsed discrete-time energy output rendering increased working velocities with an at least equal stroke but with substantially lower repetition frequencies than those of the prior art drives, without restricting the desired application functionalities by noise production, vibrations or heating-up. Moreover, the invention is in particular based on the task to provide a drive, in particular for body care apparatuses and/or body treatment apparatuses, like for example shaver apparatuses, haircutters, beard cutters, toothbrushes and the like, which has advantageous characteristics regarding a producible movement and/or a force that is generated.

The objective is achieved according to the invention with an apparatus according to independent claim 1 by the electric linear repetitive pulsed drive being realized by a magnetic shape-memory adjustment element that is situated in an air gap of a magnetic circuit, by said adjustment element being brought into a fast expansion by a current pulse in the coil of the magnetic circuit, and by the magnetic energy, which has been stored in the ferromagnetic material of the magnetic circuit by said current pulse, being deleted in the reversal point of the working-current pulse by an inverse current pulse, for the purpose of bringing the adjustment element back into its original position at the maximum possible speed via a reset unit, in particular a reset spring. Furthermore, the objective is in particular achieved by an electric linear repetitive pulsed drive according to claim 1. Advantageous further developments and implementations of the invention may be gathered from the further claims.

It is a substantial advantage relative to the prior art that the electric linear repetitive pulsed drive according to the invention outputs its energy in discrete-time manner, bundled in short time intervals, that is in pulses, as a result of which it is advantageously possible to output the maximum system energy for each individual pulse, at the same time especially advantageously allowing repetition frequencies down to manual single-pulse triggering.

Advantageously the electric linear repetitive pulsed drive comprises an abutment, in particular for the shape-memory adjustment element. Particularly preferably the abutment is non-magnetic. It is conceivable that the reset unit comprises the reset spring. It is further conceivable that the reset unit is embodied as the reset spring.

It is a further essential advantage achieved with respect to the prior art that each of the parameters, namely rise time, rise course, deflection, pulse duration, fall time, fall course and repetition frequency, may be set for the respective application case during manufacture or may be manually set by a user to optimize the respective, also individual, application and that, if only the repetition frequency is changed, the energy that is output per working pulse remains constant. It is in particular possible that an energy that is output per working pulse may remain constant in case of a change in repetition frequency. Furthermore it is conceivable that a rise time and/or a rise course and/or a deflection and/or a pulse duration and/or a fall time and/or a fall course and/or the repetition frequency are/is adjustable.

Another significant advantage of the implementation of the invention is achieved according to the invention in that, in particular for the purpose of minimizing a reset time of the pulsed drive, an inversely polarized current pulse, i.e. advantageously a deletion pulse, which is preferably initiated in the reversal point of the working pulse, abruptly deletes the magnetic field of the magnetic circuit, as a result of which the adjustment element is brought back to its original length by the reset spring, advantageously without hindrance and preferably at the maximum possible velocity.

A further significant advantage of the implementation of the invention is achieved according to the invention in that, for the purpose of minimizing the rise time of the pulsed drive, the reset unit comprises a further actuated magnetic shape-memory adjustment element, and thus the rise time is further improved as the hindering effect of the reset spring is omitted. In particular, in this case the reset unit does not comprise a reset spring. In particular, in this case the reset spring is substituted by the further actuated magnetic shape-memory adjustment element.

It is a further substantial advantage of the invention with respect to the prior art that it is possible to further improve the, already inherently moderate, noise production of the magnetic shape-memory adjustment element of the pulsed drive by noise-optimizing courses of the rise and fall curves of the magnetic field, thus allowing to dispense with a performance-affecting acoustic damping of the cinematics and of the housing by which the pulsed drive is encompassed. In particular, the electric linear repetitive pulsed drive comprises no damping. Moreover the electric linear repetitive pulsed drive in particular comprises no housing.

Another advantage of the invention with respect to the prior art is that in an operation of said apparatuses there is/are, relative to drives according to the prior art, substantially less noise, smaller vibrations, less heating-up and an increased service time with accumulator/battery operation, due to the discrete-time pulsed actuation of the pulsed drive.

The electric linear repetitive pulsed drive realizes the described advantages in apparatuses for a performance improvement of which a short, pulse-wise output working energy with at the same time low repetition frequencies provides an advantage.

The invention also comprises an apparatus, in particular an electric apparatus, in particular a body care apparatus and/or a body treatment apparatus, e.g. a shaver apparatus, a beard cutter, a haircutter, an epilator apparatus, a hair-removal apparatus, a pigmenting apparatus, a tattoo apparatus, a pricking apparatus, an electric toothbrush, or the like, as in particular mentioned above, with at least one electric linear repetitive pulsed drive. Advantageously the apparatus is implemented as a shaver apparatus and/or as a beard cutter.

DRAWINGS AND DESCRIPTION OF THE EXEMPLARY EMBODIMENT

In the following the invention is explained in detail by way of an exemplary embodiment, with reference to drawings, wherein it is shown in:

FIG. 1: a schematic representation of an exemplary pricking apparatus for the purpose of a stimulation therapy for organic skin, which is operated with the electric linear repetitive pulsed drive according to the invention.

Figure 2:
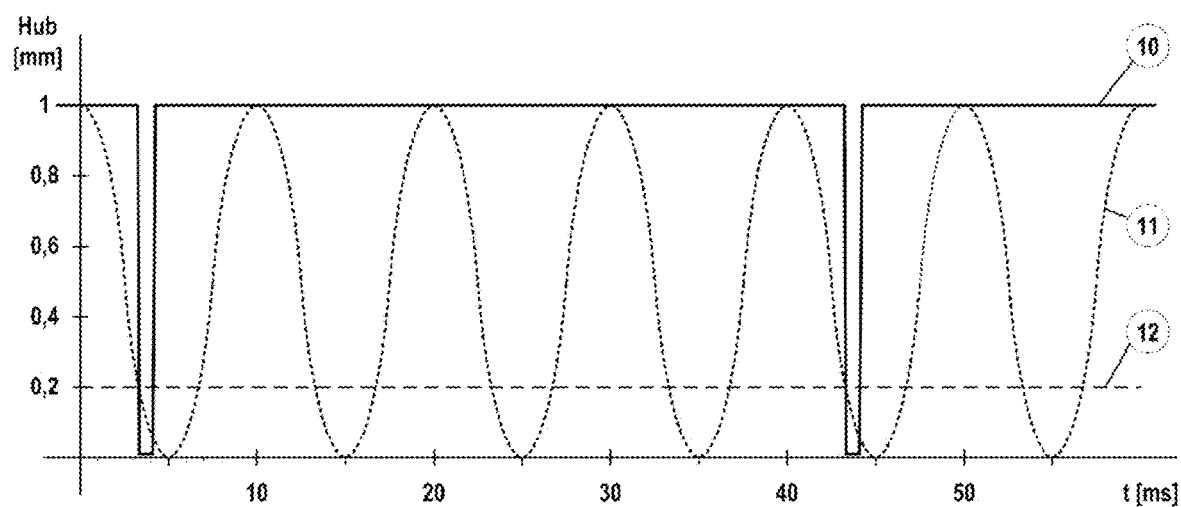

FIG. 2: path-time diagrams of the exemplary pricking apparatus operated with the pulsed drive according to the invention that is shown in FIG. 1, in comparison to a pricking apparatus having a continuous-time drive according to the prior art.

FIG. 1 exemplarily shows a pricking apparatus for stimulation therapy for organic skin, which is operated with the electric linear repetitive pulsed drive according to the invention comprising a magnetic circuit 2 with an air gap 4, an electric coil 1, a magnetic shape-memory adjustment element 5 with its non-magnetic abutment 3 and a reset unit with a reset spring 6. In particular, the reset unit is implemented as the reset spring 6. In an activation of the coil 1 by a control electronics unit 9, a magnetic field builds in the magnetic circuit 2 and the air gap 4, bringing the magnetic shape-memory adjustment element 5 into an expansion counter to the spring 6 and forcing a pricking element 8 out of a housing 7 by an amount X. When the built-up magnetic field has been deleted by an inversely polarized electric pulse, the spring 6 brings the adjustment element 5 back into its original position until the following electric working pulse occurs, such that a spectrum of repetition frequencies ranges from a standstill to a limit frequency of the drive, each pricking process having the same energy, independently from the repetition frequency. This feature is, for example, of importance for the exemplarily mentioned pricking apparatus for a stimulation therapy of organic skin, as the skin is to be pricked respectively only once in moderate path and time intervals, and this should be effected ideally always with the same energy per prick.

FIG. 2 shows path-time diagrams of the exemplary pricking apparatus, which is operated with the pulsed drive according to the invention, of FIG. 1, in comparison to a pricking apparatus with a continuous-time drive according to the prior art. A curve 10 exemplarily shows the discrete-time path-time diagram of the tip of the pricking element of the exemplary pricking apparatus for stimulation therapy, which is operated via the pulsed drive according to the invention with a pulse width of 1 ms (millisecond) and a pricking depth in an organic skin of 0.2 mm, indicated by the dashed line 12. In comparison, curve 11 shows the continuous-time path-time diagram of a customary pricking apparatus according to prior art, with a frequency of 100 Hz, i.e. a period of 10 ms. It is clearly perceivable that a prick-in velocity is substantially higher with the drive according to the invention than with the pricking apparatus according to the prior art. For example, in case of a reduction of the repetition frequency of the pulsed drive according to the invention, with the pulse duration kept constant, the advantages of the pulsed drive according to the invention increase, which at the same time corresponds to a more gentle treatment of the skin. In a comparison of both systems, it is furthermore clearly discernible that the pulsed drive according to the invention provides considerable advantages in regard to a power consumption, to energy conversion efficiency regarding the pricking energy, to system-power dissipation, to vibrations and to an operating time with accumulators/batteries.

In their different embodiments, the features of the invention disclosed in the above description, in the drawings and in the claims may implement a realization of the invention individually as well as in any combination, independently from the abstract, in respective claims or their back-referencing.

In particular, as has been mentioned before, a different apparatus is conceivable, like for example a body care apparatus and/or a body treatment apparatus with a linear repetitive pulsed drive. In particular, a shaver apparatus and/or haircutter and/or beard cutter is conceivable which is implemented analogously to the pricking apparatus described.

The invention claimed is:

1. An electric apparatus, comprising:
at least one electric linear repetitive pulsed drive configured to output working pulses, the at least one electric linear repetitive pulsed drive comprising:
a magnetic circuit with an air gap and an electric coil,
a magnetic shape-memory adjustment element and a reset unit, and
a controller, wherein
the electric linear repetitive pulsed drive repetitively outputs the working pulses in discrete-time intervals,
wherein to thereby minimize a reset time of the pulsed drive, the controller is further configured to output an inversely polarized current pulse as a deletion pulse, which is initiated in the reversal point of the working pulse, to bring the magnetic shape-memory adjustment element that is situated in the air gap of the magnetic circuit into a fast expansion, wherein the current pulse abruptly deletes the magnetic field of the magnetic circuit, as a result of which the adjustment element is brought back to its original length by a reset spring of the reset unit.

2. The electric apparatus according to claim 1, wherein a rise time, a rise course, a deflection, a pulse duration, a fall time, a fall course, and a repetition frequency of the electric linear repetitive pulsed drive are settable during a manufacture or manually by a user and wherein the energy that is output per working pulse remains constant if only the repetition frequency is changed.

3. The electric apparatus according to claim 1, wherein the electric apparatus is a body care apparatus and/or a body treatment apparatus.

4. The electric apparatus according to claim 1, wherein the electric apparatus is a shaver apparatus, a beard cutter, a haircutter, an epilator apparatus, a hair-removal apparatus, a pigmenting apparatus, a tattoo apparatus, a pricking apparatus, or an electric toothbrush.

5. An electric apparatus, comprising:
an electric coil;
a magnetic circuit magnetically coupled to the electric coil, the magnetic circuit having a magnetic core with an air gap;
a magnetic shape-memory element located in the air gap of the magnetic core, the magnetic shape-memory element being deformable by a magnetic field produced from the magnetic circuit;
a controller electrically connected to the electric coil, the controller being configured to repeatedly output discrete-time pulses to elongate a length of the magnetic shape-memory element within the air gap by energizing the magnetic circuit.

6. The electric apparatus according to claim 5, wherein the controller is further configured to output inversely polarized discrete-time pulses during a reversal point of the discrete-time pulses.

7. The electric apparatus according to claim 6, further comprising
a reset spring configured to press against the magnetic shape-memory element to reset the length of the magnetic shape-memory element within the air gap.

8. The electric apparatus according to claim 5, further comprising
a reset spring configured to press against the magnetic shape-memory element to reset the length of the magnetic shape-memory element within the air gap.

9. An electric apparatus, comprising:
at least one electric linear repetitive pulsed drive configured to output working pulses, the at least one electric linear repetitive pulsed drive comprising:
a magnetic circuit with an air gap and an electric coil,
a magnetic shape-memory adjustment element and a reset unit, and
a controller, wherein
the electric linear repetitive pulsed drive repetitively outputs the working pulses in discrete-time intervals,
wherein the reset unit further comprises a further actuated magnetic shape-memory adjustment element configured to minimize a rise time of the electric linear repetitive pulsed drive, wherein the reset unit is free of a reset spring.

10. The electric apparatus according to claim 9, wherein the electric apparatus is a body care apparatus and/or a body treatment apparatus.

11. The electric apparatus according to claim 9, wherein the electric apparatus is a shaver apparatus, a beard cutter, a haircutter, an epilator apparatus, a hair-removal apparatus, a pigmenting apparatus, a tattoo apparatus, a pricking apparatus, or an electric toothbrush.

12. An electric apparatus, comprising:
at least one electric linear repetitive pulsed drive configured to output working pulses, the at least one electric linear repetitive pulsed drive comprising:
a magnetic circuit with an air gap and an electric coil,
a magnetic shape-memory adjustment element and a reset unit, and
a controller, wherein
the electric linear repetitive pulsed drive repetitively outputs the working pulses in discrete-time intervals,
wherein a noise production of the magnetic shape-memory adjustment element of the pulsed drive is reduced by noise-optimizing courses of the rise and fall curves of the magnetic field and the apparatus is without a performance-affecting acoustic damping of the cinematics and without a housing that encompasses the electric linear repetitive pulsed drive.

13. The electric apparatus according to claim 12, wherein the electric apparatus is a body care apparatus and/or a body treatment apparatus.

14. The electric apparatus according to claim 12, wherein the electric apparatus is a shaver apparatus, a beard cutter, a haircutter, an epilator apparatus, a hair-removal apparatus, a pigmenting apparatus, a tattoo apparatus, a pricking apparatus, or an electric toothbrush.

* * * * *